United States Patent [19]

Ishogai et al.

[11] 4,423,258

[45] Dec. 27, 1983

[54] PROCESS FOR PRODUCING ETHANOL

[75] Inventors: Nobuo Ishogai; Motoyuki Hosokawa; Takashi Okawa; Natsuko Wakui; Toshiyasu Watanabe, all of Niigata, Japan

[73] Assignee: Agency of Industrial Science and Technology, Tokyo, Japan

[21] Appl. No.: 426,140

[22] Filed: Sep. 28, 1982

[30] Foreign Application Priority Data

Feb. 8, 1982 [JP] Japan .................................. 57-17411

[51] Int. Cl.³ ........................ C07C 31/08; C07C 29/00
[52] U.S. Cl. .................................................. 568/902
[58] Field of Search ...................................... 568/902

[56] References Cited

U.S. PATENT DOCUMENTS

| | | | |
|---|---|---|---|
| 4,111,837 | 9/1978 | Taylor | 568/902 |
| 4,133,966 | 1/1979 | Pretzer et al. | 568/902 |
| 4,205,190 | 5/1980 | Gane et al. | 568/902 |
| 4,319,056 | 3/1982 | Gane et al. | 568/902 |
| 4,346,179 | 8/1982 | Sugier et al. | 568/902 |

FOREIGN PATENT DOCUMENTS

| | | | |
|---|---|---|---|
| 3876 | 9/1979 | European Pat. Off. | 568/902 |
| 57-81421 | 5/1982 | Japan | 568/902 |

*Primary Examiner*—J. E. Evans
*Attorney, Agent, or Firm*—Browdy and Neimark

[57] ABSTRACT

A process for producing ethanol which comprises reacting methanol, carbon monoxide and hydrogen, characterized in that the reaction is carried out in the presence of (a) an inert solvent and (b) a catalyst containing cobalt compound, a manganese compound and a tertiary phosphine. According to the present invention, amount of by-products formed is small.

13 Claims, No Drawings

PROCESS FOR PRODUCING ETHANOL

BACKGROUND OF THE INVENTION

This invention relates to a process for producing ethanol from methanol, carbon monoxide and hydrogen.

It is known in Japanese Patent Publication (Kokai) No. 149213/1976 that ethanol was produced by reacting methanol, carbon monoxide and hydrogen in the presence of a cobalt-halide-tertiary phosphine catalyst. It was also known in British Pat. No. 2,036,739 that ethanol was produced by reacting methanol, carbon monoxide and hydrogen in the presence of a catalyst comprising cobalt, other metal belonging to Group VIII of the Periodic Table, iodine or bromine and a tertiary phosphine. According to this prior methods, many by-products, such as dimethyl ether, methyl ethyl ether, acetaldehyde, dimethoxy ethane, acetic acid, methyl acetate, ethyl acetate, methyl formate and compounds having $C_3$ or more were produced together with ethanol. That is, selectivity to neat ethanol was insufficient in the prior methods. In addition, complicated operation was necessary in the prior methods for separating ethanol from the reaction mixture.

SUMMARY OF THE INVENTION

The present inventors carried out research for overcoming the shortcomings mentioned above. We found a process for producing ethanol in which amount of by-products formed is small and selectivity to ethanol is high.

This invention relates to a process for producing ethanol which comprises reacting methanol, carbon monoxide and hydrogen, characterized in that the reaction is carried out in the presence of (a) at least inert solvent and (b) a catalyst containing at least one cobalt compound, at least one manganese compound and at least one tertiary phosphine.

The cobalt compounds include, for example, cobalt carbonyls, such as dicobalt octacarbonyl and cobalt hydride tetracarbonyl. Synthetic solutions obtained by reacting an inorganic cobalt compound, such as cobalt hydroxide, cobalt carbonate, basic cobalt carbonate or cobalt halide or an organic cobalt compound, such as cobalt organic acid salts cobaltocene or cobalt acetyl acetonate with synthesis gas containing $H_2$ and CO in methanol, or synthesis solutions obtained by reacting the inorganic cobalt compound or the organic cobalt compound with synthesis gas in the presence of a tertiary phosphine and a hydrocarbon solvent or an ether solvent can also be used as the cobalt compound constituting the catalyst. The cobalt compound may be used alone or as a mixture. Dicobalt octacarbonyl is preferable.

The amount of the cobalt compound employed may be in the range of 1–300 mg-atom, preferably 5–100 mg-atom in terms of cobalt per 1 mol of methanol. When the amount of cobalt compound is less than the lower limit mentioned above, though the reaction proceeds, the reaction speed is lowered. The use of cobalt compound in an amount of more than the upper limit merely adds to production cost.

The manganese compounds include, for example, inorganic manganese compounds, such as manganese dioxide, manganese carbonate, or manganese halides; organic acid salt of manganese, such as manganese acetate; organic manganese compounds, such as manganese acetyl acetonate; and manganese carbonyl. Manganese chloride is preferable.

The amount of the manganese compound employed may be in the range of 0.1–100 mg-atom, preferably 1–30 mg-atom in terms of manganese per 1 mol of methanol.

The tertiary phosphines of the present invention include, for example, tri-n-butyl phosphine, triphenyl phosphine, tri-p-tolylphosphine, tricyclohexyl phosphine, 1,4-bisdiphenyl phosphinobutane and 1,6-bisdiphenyl phosphinohexane. Tri-n-butyl phosphine is preferable.

The amount of the tertiary phosphine employed may be in the range of 2–600 mg-atom, preferably 10–200 mg-atom in terms of phosphorous per 1 mol of methanol. The use of the tertiary phosphine in an amount of less than the lower limit as mentioned above is less effective for suppressing formation of ethers and esters. The use of tertiary phosphine in an amount of more than the upper limit lowers the reactivity of the methanol and selectivity to ethanol.

The atomic ratio of Co:Mn:P in the catalyst of this invention may be in the range of 1:from 0.01 to 0.5:from 0.1 to 2, preferably 1:from 0.05 to 0.4:from 0.5 to 1.5. The catalysts with proportions outside the above ranges increase formation of by-products, such as ethers, esters and high boiling point products.

The inert solvent in the present invention means the one which does not have a bad effect on the reaction. The inert solvents include, for example, hydrocarbon solvents or ether solvents. Hydrocarbon solvents include, for example, aromatic hydrocarbons, such as toluene, benzene and xylene; aliphatic hydrocarbons, such as hexane and octane; and alicyclic hydrocarbons, such as cyclohexane. Toluene is particularly preferable. The ether solvents include, for example, diethyl ether, diisopropyl ether, dioxane and tetrahydrofuran. The solvent may be used alone or as a mixture.

According to this invention, high selectivity to ethanol can be achieved in the absence of an iodine component which was thought to be critical in the prior methods. An iodine component may be present in the reaction system to increase the reaction speed.

The amount of inert solvent employed may be in the range of 0.01–5 mol, preferably 0.1–2 mol per 1 mol of methanol. Use of solvent in an amount of less than the above lower limit decreases the selectivity to ethanol. Use of solvent in an amount of more than the above upper limit lowers the space time yield of ethanol and is not practical.

Carbon monoxide and hydrogen may be used in an amount of more than the stoichiometric amount of methanol. The molar ratio of CO to $H_2$ employed may be in the range of 4:1 to 1:4, preferably 2:1 to 1:3.

The reaction pressure may be in the range of more than 50 kg/cm$^2$, and preferably, the pressure is in the range of 150–450 kg/cm$^2$ in the practice of the present invention.

Carbon monoxide and hydrogen employed in the present invention may contain argon, nitrogen, carbon dioxide, methane, ethane and other inert gases. In this case, the total partial pressure of each of carbon monoxide and hydrogen is within the above reaction pressure.

The reaction temperature depends on the catalyst employed and other reaction conditions. In general, the temperature may be in the range of 150°–300° C., preferably 200°–260° C. Though the reaction proceeds at a temperature below 150° C., the reaction speed is low; at temperatures above 300° C. by-products forms.

The present invention can be carried out either as batch process or as a continuous process.

The present invention is further illustrated by non-limiting Examples and Comparative Run.

In the following Examples and Comparative Run, reactivity of methanol, selectivity to ethanol, substantial reactivity of methanol and selectivity to realizable ethanol are expressed by the following equations:

Reactivity of methanol (%) =

$$\frac{\text{mol of CH}_3\text{OH fed} - \text{mol of unreacted CH}_3\text{OH}}{\text{mol of CH}_3\text{OH fed}} \times 100$$

Selectivity to each product (%) =

$$\frac{\text{mol of CH}_3\text{OH converted to each product}}{\text{mol of CH}_3\text{OH fed} - \text{mol of unreacted CH}_3\text{OH}} \times 100$$

Substantial reactivity of methanol (%) =

$$\frac{\text{mol of CH}_3\text{OH fed} - \text{mol of unreacted CH}_3\text{OH} - \text{mol of CH}_3\text{OH converted}^{*1}}{\text{mol of CH}_3\text{OH fed}} \times 100$$

Selectivity to realizable ethanol (%) =

$$\frac{\text{mol of CH}_3\text{OH converted to realizable C}_2\text{H}_5\text{OH}^{*2}}{\text{mol of CH}_3\text{OH fed} - \text{mol of unreacted CH}_3\text{OH} - \text{mol of CH}_3\text{OH converted}} \times 100$$

*[1]contains components, such as dimethoxy methane, methyl esters, etc. from which methanol can easily be recovered through hydrolysis.
*[2]contains neat ethanol and components, such as acetaldehyde, dimethoxy ethane, ethyl esters, etc., from which ethanol can easily be recovered through hydrogenation or hydrolysis.

EXAMPLE 1

Into a shaking type 100 ml autoclave made of stainless steel were charged 10 gram (g) (0.3121 mol) of methanol, 2 g (0.0058 mol) of dicobalt octacarbonyl, 0.5 g (0.0025 mol) of manganese chloride dihydrate, 3 g (0.0148 mol) of tri-n-butyl phosphine and 10 g (0.1086 mol) of toluene. Mixed gas of $H_2$ and CO (molar ratio of 1:1) was fed to pressure of 200 kg/cm². The reaction was carried out at 230° C. for 3 hours.

After the reaction, the autoclave was cooled and the gas remaining inside the autoclave was discharged to atmospheric pressure. Gas Chromatograph (GC) Analysis (internal standard method) showed reactivity of methanol of 22.5% and selectivity to neat ethanol of 73.4%. Selectivity to each of the following components was as follows:

| methyl formate | 1.0% |
| methyl ethyl ether | 3.5% |
| methyl acetate | 1.4% |
| dimethoxy ethane | trace |

This shows substantial reactivity of methanol of 21.8% and selectivity to realizable ethanol of 80.7%.

EXAMPLE 2

The procedure of Example 1 was repeated except that 0.5 g (0.0041 mol) of diamanganese decacarbonyl was used in place of manganese chloride dihydrate. The results were as follows:

| reactivity of methanol | 33.2% |
| selectivity to neat ethanol | 70.1% |
| selectivity to methyl formate | 0.3% |
| selectivity to methyl ethyl ether | 3.3% |
| selectivity to methyl acetate | 0.4% |
| selectivity to dimethoxy ethane | trace |

This shows substantial reactivity of methanol of 32.6% and selectivity to realizable ethanol of 74%.

EXAMPLE 3

The procedure of Example 1 was repeated except that 2 g (0.0058 mol) of dicobalt octacarbonyl, 0.5 g (0.0025 mol) of manganese chloride dihydrate, 0.5 g (0.002 mol) or iodine, 3 g (0.0148 mol) of tri-n-butyl phosphine and 10 g (0.1086 mol) of toluene were charged into the autoclave of Example 1 and the reaction was carried out at 230° C. for 1 hour. The results were as follows:

| reactivity of methanol | 30.5% |
| selectivity to neat ethanol | 70.6% |
| selectivity to methyl formate | 0.3% |
| selectivity to methyl ethyl ether | 4.5% |
| selectivity to methyl acetate | 2.1% |
| selectivity to dimethoxy ethane | 3.5% |

This shows substantial reactivity of methanol of 28.4% and selectivity to realizable ethanol of 82.2%.

EXAMPLES 4–6

Into an autoclave made of stainless steel were charged 10 g (0.3121 mol) of methanol, 2 g (0.0058 mol) of dicobalt octacarbonyl, 0.5 g (0.0025 mol) of manganese chloride dihydrate, 3 g (0.0148 mol) of tri-n-butyl phosphine and each of n-octane (Example 4), cyclohexane (Example 5) and dioxane (Example 6) in an amount as shown in Table. Mixed gas of $H_2$ and CO (molar ratio of 1:1) was fed to pressure of 200 kg/cm². The reaction was carried out at 230° C. for 3 hours.

After the reaction, the autoclave was cooled and the gas remaining inside the autoclave was discharged to atmospheric pressure. GC analysis (internal standard method) gave the results as shown in Table 1.

TABLE 1

| | | Example 4 | Example 5 | Example 6 |
|---|---|---|---|---|
| solvent | kind | n-octane | cyclo-hexane | dioxane |
| | g (mol) | 10 (0.0875) | 10 (0.1188) | 10 (0.1135) |
| reactivity of methanol % | | 21.3 | 21.0 | 32.2 |
| substantial reactivity of methanol % | | 20.1 | 19.4 | 30.8 |
| selectivity to each component (%) | neat ethanol | 69.7 | 71.3 | 71.0 |
| | methyl formate | 1.5 | 1.4 | 0.7 |
| | methyl acetate | 0.7 | 0.7 | 0.8 |
| | methyl ethyl ether | 1.1 | 1.6 | 1.5 |
| | dimethoxy ethane | 3.6 | 4.9 | 1.5 |
| | realizable ethanol | 76.7 | 82.5 | 80.1 |

COMPARATIVE RUNS 1-4

The procedures of Example 1 were repeated except that the components given in Table 2 and the reaction conditions given in Table 2 were employed. The results are shown in Table 2. The lack of four components (cobalt component, manganese component, phosphine and solvent) gives inferior result to use of four components (Example 1) with respect to selectivity to neat ethanol and realizable ethanol.

TABLE 2

| | | Comp. Run 1 | Comp. Run 2 | Comp. Run 3 | Comp. Run 4 |
|---|---|---|---|---|---|
| $Co_2(CO)_8$ | g (mol) | 2 (0.0058) | 2 (0.0058) | 2 (0.0058) | 2 (0.0058) |
| $MnCl_2.2H_2O$ | g (mol) | — | — | 0.5 (0.0025) | 0.5 (0.0025) |
| tri-n-butyl phosphine | g (mol) | 3 (0.0148) | 3 (0.0148) | 3 (0.0148) | — |
| toluene | g (mol) | 10 (0.1086) | — | — | 10 (0.1086) |
| reactivity of methanol % | | 28.7 | 6.2 | 23.2 | 8.2 |
| substantial reactivity of methanol % | | 26.3 | 4.9 | 21.7 | 6.7 |
| selectivity to each component (%) | neat ethanol | 56.3 | 37.9 | 56.3 | 16.5 |
| | methyl formate | 7.0 | 21.0 | 1.1 | 5.1 |
| | methyl acetate | 0.6 | 1.1 | 2.3 | 2.8 |
| | methyl ethyl ether | 2.7 | 0.8 | 4.4 | 7.0 |
| | dimethoxy ethane | — | — | 5.1 | — |
| | realizable ethanol | 63.3 | 49.4 | 64.8 | 23.5 |

What is claimed is:

1. A process for producing ethanol which comprises reacting methanol, carbon monoxide and hydrogen, characterized in that the reaction is carried out in the presence of (a) at least one inert solvent and (b) a catalyst containing at least one cobalt compound, at least one manganese compound and at least one tertiary phosphine.

2. The process as defined in claim 1 wherein the cobalt compound is dicobalt octacarbonyl.

3. The process as defined in claim 1 wherein the manganese compound is manganese chloride.

4. The process as defined in claim 1 wherein the tertiary phosphine is tri-n-butyl phosphine.

5. The process as defined in claim 1 wherein the solvent is toluene.

6. The process as defined in claim 1 wherein amount of the cobalt compound employed is in the range of 1-300 milligram atoms in terms of cobalt per 1 mol of methanol.

7. The process as defined in claim 1 wherein amount of the manganese compound employed is in the range of 0.1-100 milligram atoms in terms of manganese per 1 mol of methanol.

8. The process as defined in claim 1 wherein amount of the tertiary phosphine employed is in the range of 2-600 milligram atoms in terms of phosphorus per 1 mol of methanol.

9. The process as defined in claim 1 wherein atomic ratio of cobalt:manganese:phosphorus in the catalyst is in the range of 1:from 0.01 to 0.5:from 0.1 to 2.

10. The process as defined in claim 1 wherein solvent is used in amount of 0.01-5 mol per 1 mol of methanol.

11. The process as defined in claim 1 wherein carbon monoxide and hydrogen are used in an amount of more than the stoichiometric amount of methanol.

12. The process as defined in any one of claims 1-11 wherein the reaction pressure is in the range of 50-450 $Kg/cm^2$.

13. The process as defined in any one of claims 1-11 wherein the reaction temperature is in the range of 150°-300° C.

* * * * *